United States Patent
Kamakura et al.

(10) Patent No.: US 10,515,716 B2
(45) Date of Patent: Dec. 24, 2019

(54) CLINICAL RESEARCH INFORMATION CLOUD SERVICE SYSTEM AND CLINICAL RESEARCH INFORMATION CLOUD SERVICE METHOD

(71) Applicant: AGATHA INC., Tokyo (JP)

(72) Inventors: Chiemi Kamakura, Tokyo (JP); Hisashi Shimobayashi, Tokyo (JP); Guillaume Gerard, Tokyo (JP); Robert Karlsson, Tokyo (JP); Ahmed Nafkha, Tokyo (JP)

(73) Assignee: AGATHA INC., Tokyo (JP)

( * ) Notice: Subject to any disclaimer, the term of this patent is extended or adjusted under 35 U.S.C. 154(b) by 75 days.

(21) Appl. No.: 15/777,179

(22) PCT Filed: Nov. 14, 2016

(86) PCT No.: PCT/JP2016/083731
§ 371 (c)(1),
(2) Date: May 17, 2018

(87) PCT Pub. No.: WO2017/086276
PCT Pub. Date: May 26, 2017

(65) Prior Publication Data
US 2018/0350449 A1 Dec. 6, 2018

(30) Foreign Application Priority Data

Nov. 18, 2015 (JP) .................................. 2015-225622

(51) Int. Cl.
*G16H 10/20* (2018.01)
*H04L 29/06* (2006.01)

(52) U.S. Cl.
CPC ............. *G16H 10/20* (2018.01); *H04L 63/08* (2013.01); *H04L 65/1063* (2013.01); *H04L 67/42* (2013.01)

(58) Field of Classification Search
CPC ...... H04L 63/08; H04L 65/1063; G16H 10/20
See application file for complete search history.

(56) References Cited

U.S. PATENT DOCUMENTS 7,570,635 B2 * 8/2009 Gotoh ................ H04L 12/1886
370/389
8,606,599 B1 12/2013 Wong et al.
(Continued)

FOREIGN PATENT DOCUMENTS

JP 2005-310045 A 11/2005
JP 2006-215820 A 8/2006
(Continued)

OTHER PUBLICATIONS

"Cut-Do-Square," Japan Medical Association Center for Clinical Trials, accessed at http://www.jmacct.med.or.jp/cds/apply.html, pp. 2 (Oct. 25, 2015).
(Continued)

*Primary Examiner* — El Hadji M Sall
(74) *Attorney, Agent, or Firm* — Maschoff Brennan

(57) ABSTRACT

A data conversion server mutually converts a structure of a communication data transmitted and received between a data transfer server and an application server, based on a metadata which makes a structure of a communication data defined for each research client system associate with a structure of a communication data commonly used by a plurality of the application servers connected to a researcher terminal.

9 Claims, 8 Drawing Sheets

(56) References Cited

U.S. PATENT DOCUMENTS

| | | | |
|---|---|---|---|
| 2006/0100912 A1* | 5/2006 | Kumar | G06Q 40/08 705/4 |
| 2007/0168461 A1 | 7/2007 | Moore | |
| 2007/0282748 A1* | 12/2007 | Saint Clair | H04L 41/06 705/51 |
| 2008/0005054 A1* | 1/2008 | Kurian | G06Q 50/24 706/52 |
| 2010/0202447 A1* | 8/2010 | Long | H04M 3/54 370/352 |
| 2011/0131180 A1* | 6/2011 | Tuli | G06Q 10/10 707/610 |
| 2011/0153351 A1 | 6/2011 | Vesper et al. | |
| 2013/0347125 A1* | 12/2013 | Rezlan | H04L 63/1408 726/27 |
| 2014/0207935 A1* | 7/2014 | Gopshtein | H04L 43/50 709/224 |
| 2015/0301839 A1* | 10/2015 | Bansal | H04L 67/06 709/222 |

FOREIGN PATENT DOCUMENTS

| | | |
|---|---|---|
| JP | 2008-511934 A | 4/2008 |
| JP | 2009-265741 A | 11/2009 |
| WO | 2006/026673 A2 | 3/2006 |
| WO | 2015/118878 A1 | 8/2015 |

OTHER PUBLICATIONS

Extended European Search Report dated May 27, 2019 as received in Application No. 16866278.1.

* cited by examiner

FIG. 4

⟨Page for Medical Research Institutions and Researchers⟩

| Document Management | Name of Document | Date of Update | Status |
|---|---|---|---|
| ■ AAA Test | | | |
| ■ Bbbbb | Abcde audit plan, Abcde audit report, Abcde implementation plan, Abcde summary report | 2014/09/05 | Approved |
| ■ Ccccc | Abcde audit plan, Abcde audit report, Abcde implementation plan, Abcde summary report | 2014/10/02 | Reviewed |
| ■ Ddddd | Abcde audit plan, Abcde audit report, Abcde implementation plan, Abcde summary report | 2014/09/01 | Approved |
| ■ Eeeee | Abcde audit plan, Abcde audit report, Abcde implementation plan, Abcde summary report | 2014/10/30 | Created |

| Task | Time Limit |
|---|---|
| Upload your resume. | 2015/10/07 |
| Check safety information. | 2015/10/06 |
| Approve BB report. | 2015/10/10 |

News
- The XXX-th IRB is held on 10/25.
- The YYY in XXX plan document is modified.
- Carry-in date of clinical research drug is scheduled on XX.

Information from Companies
- Application is invited for CCCC clinical research.
- Attachment to BBB is revised.
- XXX seminar is held on 10/25.

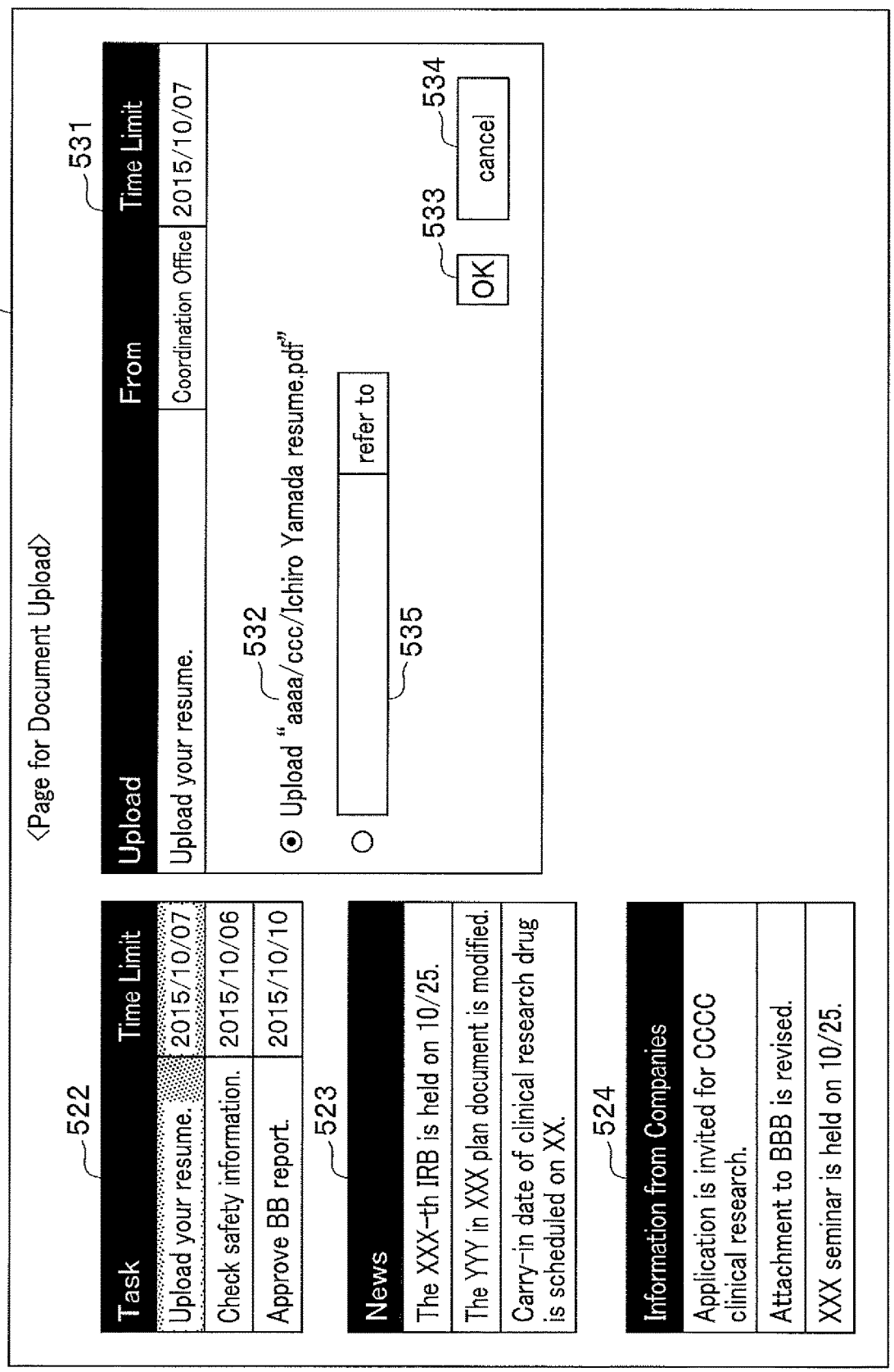

CLINICAL RESEARCH INFORMATION CLOUD SERVICE SYSTEM AND CLINICAL RESEARCH INFORMATION CLOUD SERVICE METHOD

TECHNICAL FIELD

The present invention relates to a clinical research information cloud service system and a clinical research information cloud service method which support clinical research operations.

BACKGROUND ART

A clinical research which includes a clinical trial of a newly-developed medicine or medical equipment is usually performed jointly by a medical research institution, a hospital, a pharmaceutical manufacturer, a medical equipment manufacturer, or the like. In order to achieve such a clinical research efficiently and smoothly, those who take part in the clinical research need to share various information among them. The Japan Medical Association provides, for example, a cloud clinical trial operation support system as a tool for sharing information on a clinical trial (or the like) in an attempt to improve efficiency of a clinical research, which is called "Cut-Do-Square" (see Non-Patent Document 1). The Cut-Do-Square system unifies formats of documents created by: a research client of a clinical research such as a pharmaceutical manufacturer and a medical equipment manufacturer; an entity which performs a clinical research, such as a research institution and a hospital; a subject of a clinical research, or the like. The system also supports sharing and managing the created documents therebetween.

Patent Document 1 discloses an example of a clinical research management system for efficiently executing a clinical trial in a medical research institution, a hospital, or the like (see FIG. 1, etc.). In the clinical research management system, a clinical trial request server 1, a clinical trial execution server 2, and execution organization servers 3, 4, 5, which are connected to each other via a network, supports various tasks executed by a doctor, a clinical research coordinator, or any others involved in a clinical trial of interest. As will be understood, the support includes management of information exchange among a client, a doctor, and a clinical research coordinator of the clinical trial, and management of documents.

RELATED ART DOCUMENTS

Patent Document

Patent Document 1: Japanese Laid-Open Patent Application, Publication No. 2006-215820 (to be referred to as Patent Document 1 hereinafter)

Non-Patent Document

Non-Patent Document 1: "Cut-Do-Square", [online], Japan Medical Association Center for Clinical Trials, [searched on Oct. 20, 2015], Internet <URL: http://www.j-macct.med.or.jp/cds/apply.html>

SUMMARY OF THE INVENTION

Problem to be Solved by the Invention

In many cases, a clinical research such as a clinical trial is performed involving not only a large-sized medical research institution or general hospital but also a small-sized local hospital. Such a large medical research institution or general hospital may introduce the clinical research management system as disclosed in Patent Document 1, and can thereby reduce workload of a researcher, a doctor, or a clinical research coordinator. Such an introduction and an operation thereafter of the clinical research management system require, however, a significant cost, which a small hospital may not necessarily afford.

The problem described above may be solved by renting a terminal of a clinical research management system owned by a clinical research client or the like, to a small hospital. Not a few small hospitals may be, nonetheless, offered requests for performing clinical trials from a plurality of clinical research clients. In that case, the small hospital needs to separately install respective terminals of different clinical research management systems for each of a plurality of clinical research clients. A doctor or a clinical research coordinator of the hospital is required to be familiarized with an operation method of each of a plurality of the different terminals. This imposes a heavy burden on the doctor or the clinical research coordinator.

The "Cut-Do-Square" provided by the Japan Medical Association is a system which can be used on a generally-available personal computer connected to the Internet for free of charge. With the Cut-Do-Square, a document can be easily created and the created document can be shared among persons in charge of research of a specific clinical trial project, though the document or information which can be shared is limited to that created in accordance with a previously registered uniform format. A doctor or a clinical research coordinator even in a small hospital can therefore use the system easily.

A major function of the Cut-Do-Square is nonetheless creation of a document in accordance with a standard format and management of the created document. A supporting function is still not necessarily sufficient for making various types of information produced in an ordinary clinical research on a day-to-day basis sharable especially between a person in charge of the clinical research and a research client thereof. It is thus difficult especially for a doctor or a clinical research coordinator in a small hospital in charge of clinical researches from a plurality of research clients to expect sufficient improvement in operation efficiency from the Cut-Do-Square.

A clinical research such as a clinical trial is generally implemented such that a plurality of clinical research projects from a plurality of research clients (such as a pharmaceutical manufacturer) are concurrently performed. In that case, a person in charge of the clinical research such as a doctor, a pharmacist, a research coordinator, or the like is required to receive documents in different formats varying with different research clients and create respective report documents in accordance with the different formats. Such circumstances impose a heavy burden on the person in charge of the clinical research, and prevent improvement in efficiency of research operations.

The present invention has been made in light of the problems in the related art as described above and in an attempt to provide a clinical research information cloud service system and a clinical research information cloud service method which, even when a person is in charge of a plurality of clinical research projects of a plurality of research clients progress concurrently, a workload of the person in charge can be prevented from increasing.

Means for Solving the Problem

A clinical research information cloud service system includes: a plurality of application servers which are installed respectively corresponding to a plurality of clinical research projects and which are connected to a researcher terminal used by a person in charge of research of the clinical research project, via a communication network; a plurality of data transfer servers which are connected respectively corresponding to a plurality of research client systems used by respective research clients of a plurality of the clinical research projects; and a data conversion server which are connected to both a plurality of the data transfer servers and a plurality of the application servers and which includes a metadata for mutually associating a structure of a first communication data defined for each of a plurality of the research client systems and a structure of a second communication data commonly used by a plurality of the application servers, the data conversion server configured to, by referencing the metadata, mutually convert structures of the first and second communication data transmitted and received between the data transfer server and the application server.

Advantageous Effects of the Invention

The present invention provides a clinical research information cloud service system and a clinical research information cloud service method which, even when a person is in charge of a plurality of clinical research projects of a plurality of research clients progress concurrently, a workload of the person in charge can be prevented from increasing.

BRIEF DESCRIPTION OF THE DRAWINGS

FIG. 4 is a diagram illustrating an example of a landing page displayed in the researcher terminal after login.

FIG. 5 is a diagram illustrating an example of a document upload page.

EMBODIMENT FOR CARRYING OUT THE INVENTION

Figure 1:
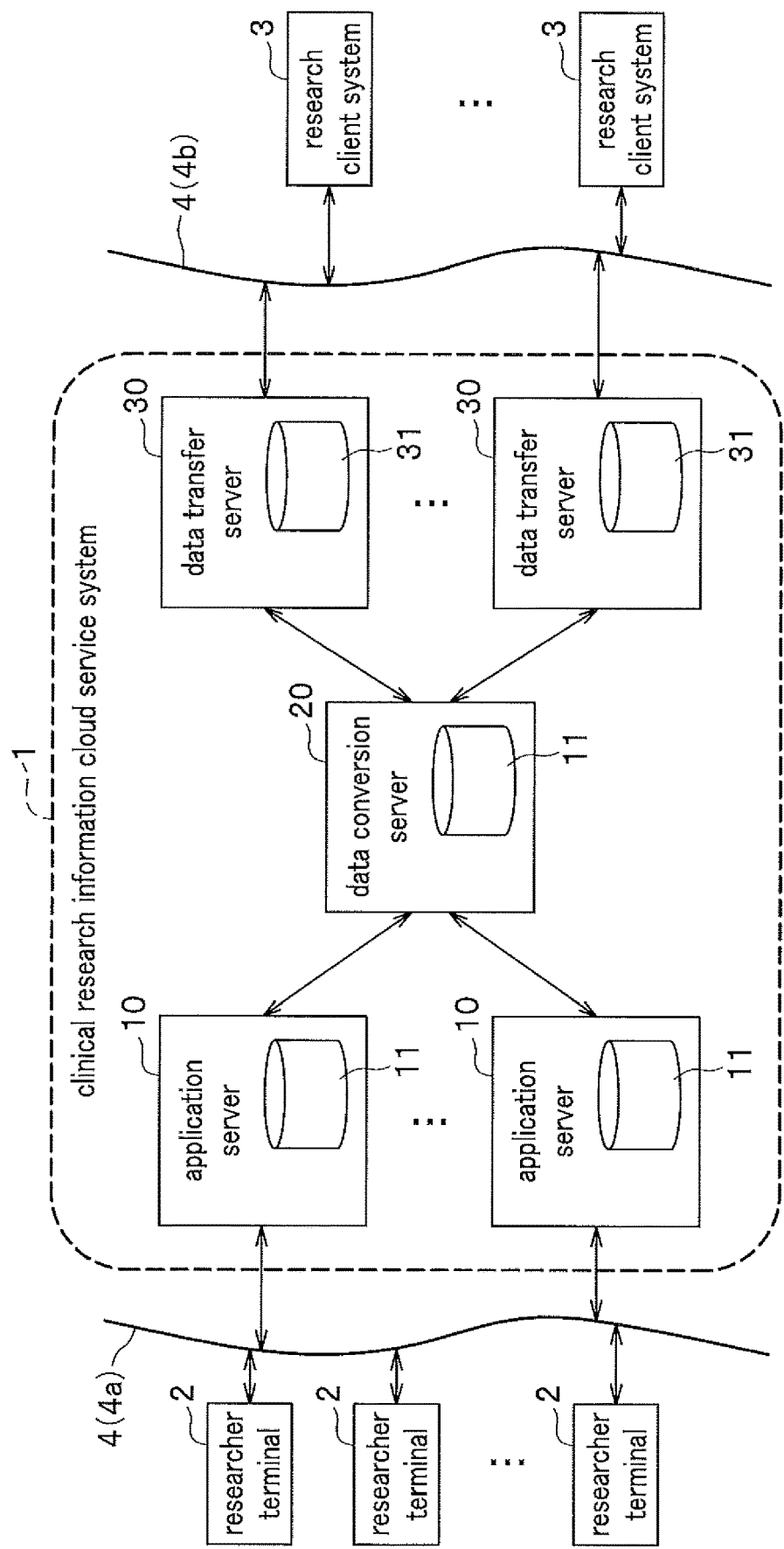
FIG. 1 is a diagram illustrating an example of an entire configuration of a clinical research information cloud service system according to an embodiment of the present invention.

An embodiment of the present invention is described below in detail with reference to related drawings. In each of the related figures, the same reference numerals are given to the same components and description thereof is omitted herefrom.

FIG. 1 is a diagram illustrating an example of an entire configuration of a clinical research information cloud service system 1 according to an embodiment of the present invention. As illustrated in FIG. 1, the clinical research information cloud service system 1 includes an application server 10, a data conversion server 20, and a data transfer server 30. A researcher terminal 2 used herein is a generally-available computer or the like used by a person in charge of a clinical research such as a researcher, a doctor, a pharmacist, and a research coordinator (to be collectively referred to as a person in charge of research hereinafter). A research client system 3 used herein is a system for supporting a clinical research on a prescribed subject, adopted in-house in a client who requests the clinical research, such as a pharmaceutical manufacturer and a medical equipment manufacturer.

The application server 10: is connected to a plurality of the researcher terminals 2 via a communication network 4a; and supports tasks related to a clinical research performed by a researcher, via a web browser screen displayed in a display device of the researcher terminal 2. That is, the application server 10: supports transfer of information from a research client of a clinical research on a prescribed subject (which may also be referred to as a research project hereinafter) to a person in charge of the research; and facilitates communication between the research client and the person in charge of the research. The application server 10 also: supports sharing of information or documents among researchers belonging to the same research project; and improves operational efficiency.

One unit of the application server 10 is typically installed for each research project. It is assumed herein, however, that the application server 10 provides, however, the same function to each of the researcher terminals 2, even if a research project of interest is different. That is, the web browser screen displayed in the researcher terminal 2 basically has the same configuration independently of the research project of interest. Note that an example of the web browser screen displayed in the researcher terminal 2 will be described later with reference to the related drawings.

The application server 10 includes a storage unit 11. The storage unit 11 stores therein information or document data which is to be shared by all persons or some persons for each group in charge of a research project of interest. Note that the storage unit 11 may store therein, for example, data of a document which is prepared by a person in charge of the research project by himself/herself and is not intended to be shared with others, such as a document still in process of preparation.

The person in charge of research can gain access to information or a document shared for each research project, via the researcher terminal 2, by logging in to the appropriate application server 10 associated with each research project. At this time, the person in charge of research can use any researcher terminal 2 as long as the researcher terminal 2 is connected to the communication network 4a. Even when the person in charge of research takes part in a plurality of research projects, the person in charge can simply use the same researcher terminal 2 (for example, his/her own PC). In addition, the person in charge can use the researcher terminal 2 with similar operations on similar display screens for different research projects.

The data transfer server 30 is connected to the research client system 3 introduced in a research client of interest, via a communication network 4b; and is also connected to the data conversion server 20. The data transfer server 30: receives information transmitted from the research client system 3; transfers the received information to the data conversion server 20; and transmits the information transferred from the data conversion server 20, to the research client system 3.

When a plurality of the research client systems 3 are present, one unit of the data transfer server 30 is set up corresponding to each of a plurality of the research client systems 3. This makes it possible for each data transfer server 30 to transmit and receive data using or in accordance with a communication procedure defined by the research client system 3.

The data transfer server 30 includes a storage unit 31. The storage unit 31 temporarily stores therein data transmitted and received between the research client system 3 and the data conversion server 20.

The data conversion server 20: is disposed between the application server 10 and the data transfer server 30; mediates transmission and reception of communication data therebetween; and converts a structure of the communication data transmitted and received therebetween. The conversion of the communication data structure used herein means that a structure of a communication data transmitted and received between the data conversion server 20 and the data transfer server 30 (that is, the research client system 3) and a structure of a communication data transmitted and received between the data conversion server 20 and the application server 10 are associated with each other and are mutually converted accordingly.

A communication data referred to as a packet, a frame, or the like, generally contains a source, a destination, an information type, or the like of the communication data. In this embodiment, the communication data also contains a name of a research project, a person in charge of the research, or the like. Different research client systems 3 may or may not differ in what kind of information is arranged in what order in a communication data or in what kind of information has what kind of bit configuration (byte configuration).

In this embodiment, in light of the described above, the data conversion server 20 converts respective communication data structures of a plurality of the research client systems 3 which are different from each other, into a structure of a communication data which can be commonly used by a plurality of the application servers 10. In order to realize the conversion, the storage unit 11 of the data conversion server 20 stores therein a so-called metadata. The data conversion server 20 converts a structure of a communication data between the two, based on reference to the metadata.

Further, the data conversion server 20: converts respective structures of communication data from a plurality of the research client systems 3 received via a plurality of the data transfer servers 30; and transmits the communication data of which structures have been converted to the application server 10 as an destination. Similarly, the data conversion server 20: converts structures of communication data from a plurality of the application servers 10; and transmits the converted communication data to the data transfer server 30 which has been associated with the research client system 3 as a destination.

Note that, in FIG. 1, the communication network 4 is illustrated such that the communication network 4a to which the researcher terminal 2 is connected is a network separate from the communication network 4b to which the research client system 3 is connected. The communication networks 4a, 4b may be, however, connected to each other. That is, the communication networks 4a, 4b may be part of the Internet or the like.

The application server 10, the data conversion server 20, and the data transfer server 30 which constitute the clinical research information cloud service system 1 as illustrated in FIG. 1 can be realized by a plurality of computers which are connected to each other via a dedicated communication line or the Internet. In this case, part or all of a plurality of the application servers 10 and a plurality of the data transfer servers 30 may be realized by a single unit of a computer. Or, all of the application server 10, the data conversion server 20, and the data transfer server 30 may be realized by a single unit of a computer.

Figure 2:
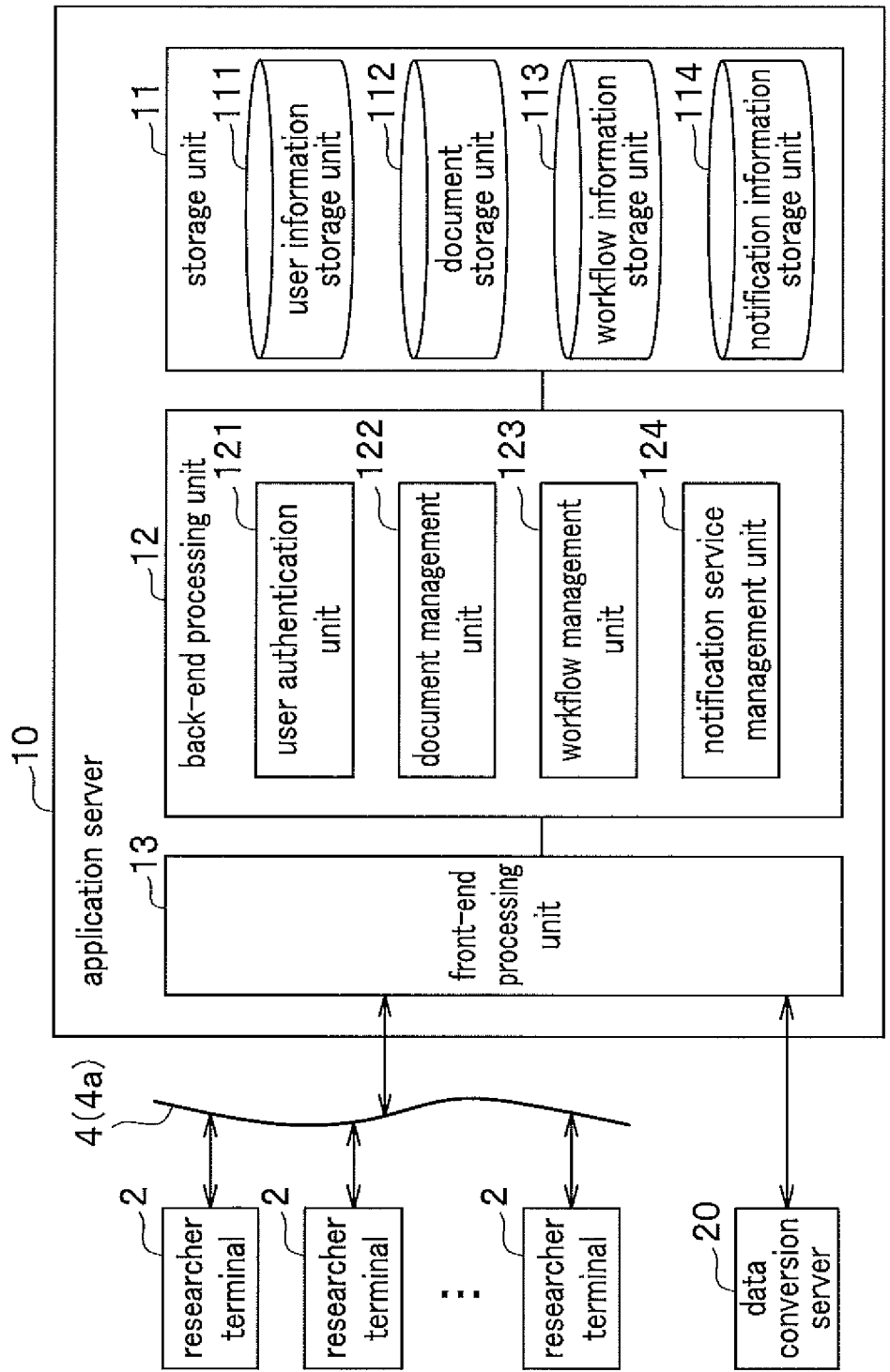
FIG. 2 is a diagram illustrating an example of a configuration of an application server in the clinical research information cloud service system according to the embodiment of the present invention.

FIG. 2 is a diagram illustrating an example of a configuration of the application server 10 in the clinical research information cloud service system 1 according to the embodiment of the present invention. As illustrated in FIG. 2, the application server 10 includes a front-end processing unit 13, a back-end processing unit 12, and the storage unit 11.

The front-end processing unit 13 mainly controls: a screen display in the researcher terminal 2 connected via the communication network 4a; and an input of data entered on the displayed screen. The front-end processing unit 13 also controls transmission and reception of communication data to and from the data conversion server 20. The back-end processing unit 12 includes a user authentication unit 121, a document management unit 122, a workflow management unit 123, and a notification service management unit 124, each of which serves as a functional block for realizing functions of the application server 10.

The user authentication unit 121 supports a user registration of a person in charge of a research project in the application server 10 of interest. The user authentication unit 121 also authenticates, when a user logs in to the application server 10, whether or not the user is a registered normal user. Note that information on a user ID, a password, or the like of a registered user is previously stored in the user authentication storage unit 111.

The document management unit 122 manages a document stored in a document storage unit 112 of the application server 10 of interest. At this time, the document is basically managed user by user, and is also managed by being categorized into such a document that can be opened to all research project members, that can be opened to group members who have been grouped together in a research project, or the like.

The workflow management unit 123: manages a person in charge, a time deadline, a progress status, or the like of preparation, review, approval, or the like of various tasks and documents; and, when the time deadline is approaching, notifies the person in charge accordingly. Note that information managed by the workflow management unit 123 is stored in a workflow information storage unit 113.

The notification service management unit 124: mainly notifies a specified user (a person in charge of research) of various types of notification information notified by the research client system 3; and, when the notification information has been read, transmits information indicating that the notification information has been read, back to an originating source (the research client system 3). The notification information: is stored in a notification information storage unit 114; and is displayed in, for example, when a user logs in to the application server 10, the researcher terminal 2 being used by the user. Note that types of the notification information include that addressed to: a specific person in charge of research; a member of a specific group; and all members of a research project.

Figure 3:
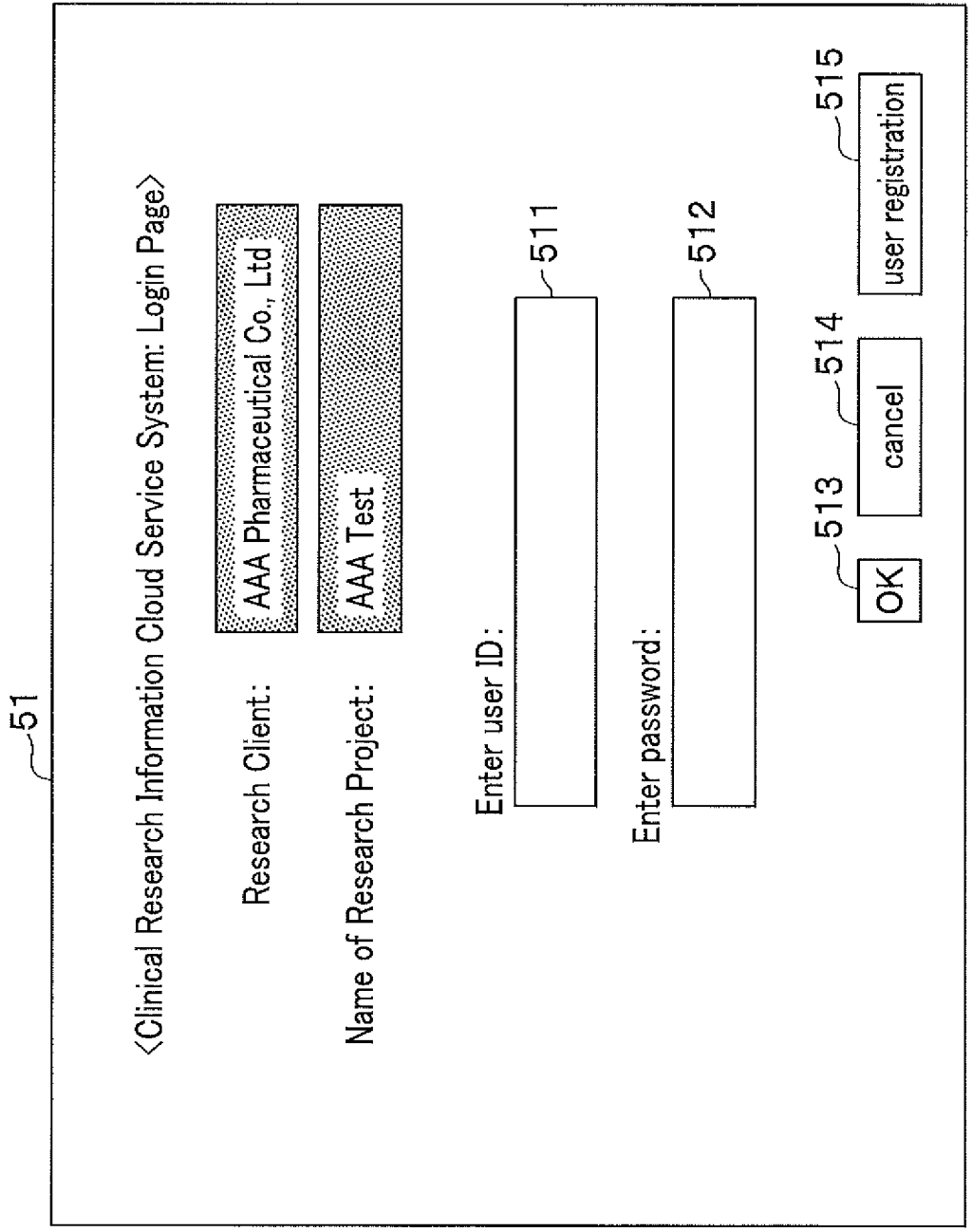
FIG. 3 is a diagram illustrating an example of a login page displayed in a researcher terminal by the application server.

FIG. 3 is a diagram illustrating an example of a login page 51 displayed in the researcher terminal 2 by the application server 10. A user (a person in charge of research) gains access to the login page 51 as illustrated in FIG. 3 via the researcher terminal 2, when the user wishes to log in to the appropriate application server 10 associated with a research project of which the user is in charge.

The login page 51 displays thereon a name of a research client of a research project associated with the application server 10 of interest and a name of the research project. The login page 51 also displays thereon input boxes 511, 512, into which a user is prompted to enter a user ID and a password, respectively.

When the user enters the user ID and the password into the input boxes 511, 512, respectively, and clicks an "OK" button 513, the authentication unit 121 determines whether or not the inputted user ID and password are those of an already-registered normal user. As a result of the determination, if the inputted user ID and password are those of an already-registered normal user, the application server 10 makes the researcher terminal 2 display a landing page 52 (see FIG. 4).

Note that, when a "cancel" button 514 on the login page 51 is clicked, the login page 51 is closed. When a "user register" button 515 is clicked, a new page for user registration (not shown) is displayed in the researcher terminal 2.

FIG. 4 is a diagram illustrating an example of the landing page 52 displayed in the researcher terminal 2 after login. As illustrated in FIG. 4, the landing page 52 displays thereon, for example, a "document management" display window 521, a "task" display window 522, a "news" display window 523, and an "information from companies" display window 524. As described above, the landing page 52 displays thereon information possibly desired by a user briefly and comprehensively.

The "document management" display window 521 displays thereon information on a document managed by the document management unit 122. How to display the document is similar to that used in a generally-available computer. A hierarchical structure of folders is displayed, and, when a folder is selected, a list including a name of a document stored in the folder, and a document revised (or created) date is displayed. Additionally, in this embodiment, information on whether or not a document managed by the workflow management unit 123 has already been created, reviewed, approved, or the like is displayed for each document as an annex to the list of the each document.

In this embodiment, a status of a workflow (such as already-created, already-reviewed, and already-approved) may be taken as a folder, using a metadata attached to the each document, and a list of documents belonging to the respective statuses may be thereby displayed. In this case, the "document management" display window 521 displays therein, for example, a folder such as "created", "reviewed", and "approved" is displayed as a lower level folder of a folder "AAA test". If, for example, the "created" as the lower level folder is selected, a list of documents each of which has the status of "created" is displayed from among the documents belonging to the folder "AAA test". Note that how to display a document as described above in which a status of a workflow is taken as a folder can also be used for a folder in any of a plurality of hierarchical levels, using a combination of metadata.

The "task" display window 522 displays therein task information which has a deadline drawing near, from among information managed by the workflow management unit 123 (to be referred to as task information hereinafter). Of the task information, information of special importance is highlighted in bold type or in red color. Note that types of the tasks include a request for upload, review, approval, and confirmation of a document.

The "news" display window 523 displays therein, from among notification information managed by the notification service management unit 124, notification information for: a person in charge of a research, during log in; a member of a group to which the person in charge of the research, during log in, belongs; and all members of the research project. Note that the notification information is typically transmitted from the research client system 3, and may be, however, transmitted from another person in charge of the research via the researcher terminal 2.

The "information from companies" display window 524 displays therein, from among the notification information managed by the notification service management unit 124, a typical type of notification information. The typical type of notification information used herein includes notification information which is notified from a research client but is not directly relevant to a research project of interest, such as, for example, recruiting of a member of a new research project. Note that the "information from companies" display window 524 may contain information transmitted from companies other than the research client of the research project of interest.

A user can select and click on any one piece of the information displayed on the "task" display window 522, the "news" display window 523, and the "information from companies" display window 524. When the user selects and clicks on any one piece of the information, a new display window (for example, see FIG. 5) appears, and the newly-appeared display window displays therein further details on the information selected by the click.

FIG. 5 is a diagram illustrating an example of a page of document upload 53. When the upload request information in the "task" display window 522 on the landing page 52 is clicked, the document upload page 53 as illustrated in FIG. 5 appears. The document upload page 53 displays thereon an "upload request" display window 531, in place of the "document management" display window 521 having been displayed on the landing page 52.

The "upload request" display window 531 displays a directory of a document to be uploaded as a default and a name of the document 532. If the displayed name of the document 532 is appropriate, the user clicks an "OK" button 533, which allows uploading of the document to be uploaded into the research client system 3. If there is any change in the directory of the document to be uploaded or the name of the document, the user enters an appropriate directory of a document to be uploaded or an appropriate name of the document into an input box 535, and then clicks the "OK" button 533. Note that if the user clicks a "cancel" button 534, the "upload request" display window 531 is closed without uploading the document.

In the "task" display window 522, when the user clicks such information as a request for creation, review, approval, or the like of a document, a new display window similar to the "upload request" display window 531 appears. When the user clicks any one piece of information from among the notification information displayed on the "news" display window 523 and the "information from companies" display window 524, a new display window (not illustrated) appears with further details of the clicked notification information.

Figure 6:
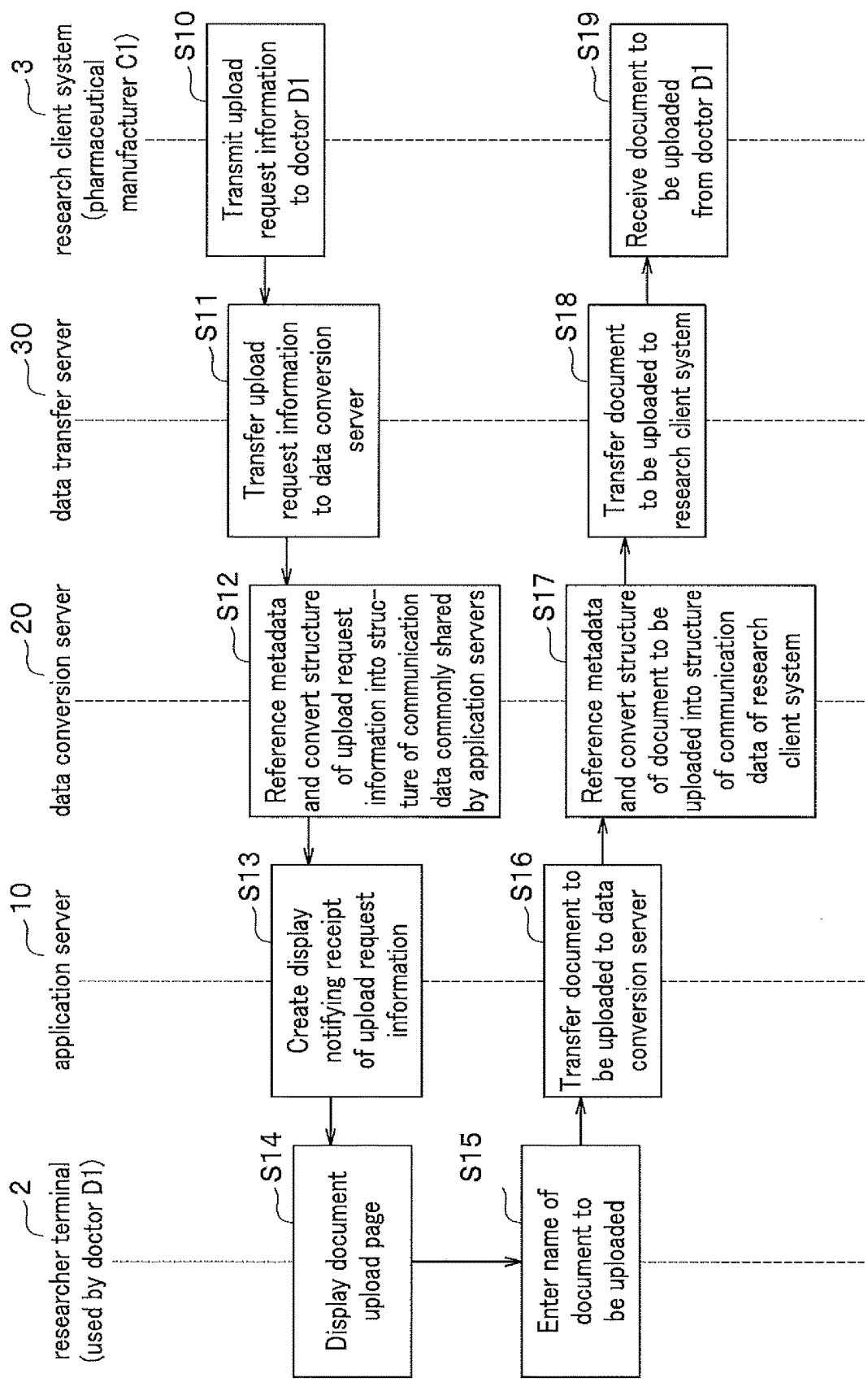
FIG. 6 is a diagram illustrating an example of a flow of an information processing performed when upload request information is transmitted from a research client system to a researcher terminal.

FIG. 6 is a diagram illustrating an example of a flow of an information processing performed when information on an upload request is transmitted from the research client system 3 to the researcher terminal 2. Description below is made with reference to FIG. 6, assuming that upload request information is transmitted from a pharmaceutical manufacturer C1 which is a research client of a research project P1, to a doctor D1 who belongs to the research project P1.

As a start, the research client system 3 of the pharmaceutical manufacturer C1 transmits upload request information to the doctor D1 who belongs to the research project P1 (step S10). The data transfer server 30 associated with the research client system 3 of the pharmaceutical manufacturer C1 receives the upload request information and transfers the received upload request information to the data conversion server 20 (step S11).

Upon receipt of the upload request information, the data conversion server 20 references metadata stored in a storage unit 21, based on which the data conversion server 20 converts a structure of the received upload request information (communication data) into a structure of a communication data commonly shared by the application servers 10 (step S12). That is, the data conversion server 20 converts information such as a destination, a source, a type of a document, or the like which are contained in the received upload request information, into information such as a destination, a source, a type of a document, or the like which are used in common by a plurality of the application servers 10.

Note that the upload request information received by the data conversion server 20 contains information indicating that the source is the pharmaceutical manufacturer C1, that the destination is the doctor D1 belonging to the research project P1, or the like, based on a structure of a communication data determined by the research client system 3 of the pharmaceutical manufacturer C1. The data conversion server 20: then checks the upload request information containing therein the above-described information against the metadata; and converts the upload request information into an identification number of the application server 10 to be used as a destination of the upload request information or a name of a person in charge of a research of interest (for example, a name of the doctor D1). The data conversion server 20 transmits the upload request information to the application server 10, taking the acquired identification number of the application server 10 or the person in charge of research (for example, the doctor D1) as a destination.

Next, the application server 10 having received the converted upload request information creates a display which is to notify, for example, the doctor D1 of the receipt of the information in the "task" display window 522 on the landing page 52 (see FIG. 4) (for example, a display of "Upload your resume." in FIG. 4) (step S13). Note that what is performed by the application server 10 herein is only preparation of the display in the "task" display window 522 notifying the receipt of the upload request information. An actual display thereof is performed by the researcher terminal 2.

When the doctor D1 logs in to the application server 10 of interest via the researcher terminal 2, the researcher terminal 2 being used by the doctor D1 displays therein the landing page 52 with the "task" display window 522 thereon. Then, if the doctor D1 clicks, for example, a display portion (see FIG. 4) saying "Upload your resume." in the "task" display window 522, the researcher terminal 2 then displays the document upload page 53 (see FIG. 5) (step S14).

When the doctor D1 enters a name of a document (including a name of a directory) to be uploaded via the document upload page 53 (step S15), the application server 10 transfers the document specified by the name thereof to the data conversion server 20, as the document to be uploaded (step S16). At this time, information such as a destination, a source, a document type, or the like is added to the document to be uploaded. The document to be uploaded (for example, a resume of the doctor D1) may be stored in the researcher terminal 2 used by the doctor D1 or in a dedicated or a shared storage area allocated to the doctor D1 of the storage unit 11 of the application server 10 for the research project P1.

The data conversion server 20 then: references the metadata stored in the storage unit 21; converts a structure of a communication data of the document to be uploaded (containing information such as a destination, a source, an information type, or the like) transmitted from the application server 10, into a structure of a communication data used in the research client system 3 as the destination (step S17); and transfers the converted document to be uploaded to the data transfer server 30.

The data transfer server 30 then transfers the document to be uploaded transferred from the data conversion server 20, to the research client system 3 specified by the destination (step S18). In this way, the research client system 3 receives the document to be uploaded from the doctor D1 to whom the uploading has been requested (step S19).

Figure 7:
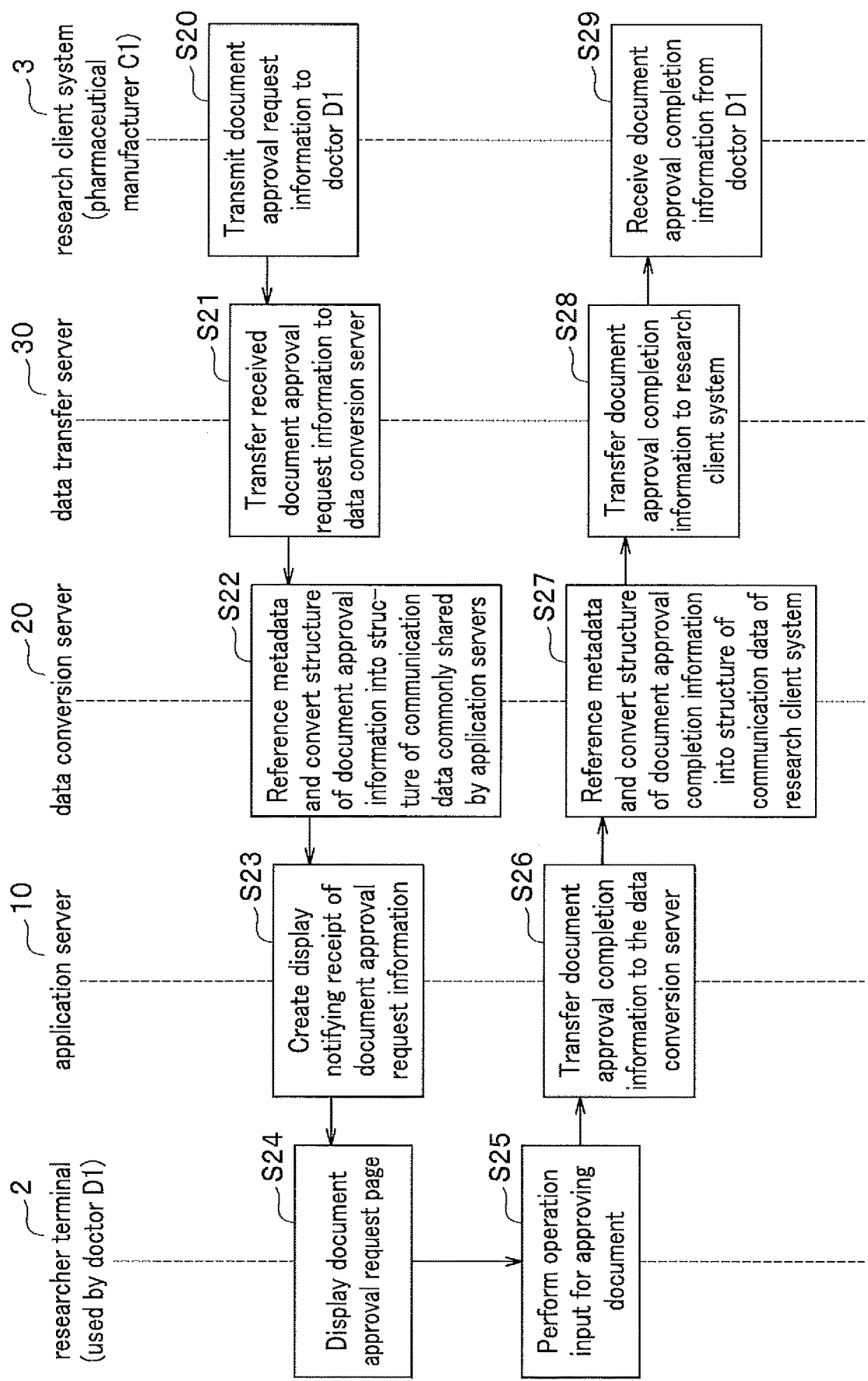
FIG. 7 is a diagram illustrating an example of a flow of an information processing performed when document approval request information is transmitted from the research client system to the researcher terminal.

FIG. 7 is a diagram illustrating an example of a flow of an information processing performed when information on a document approval request is transmitted from the research client system 3 to the researcher terminal 2. Below is described, with reference to FIG. 7, a case where document approval request information is transmitted from the pharmaceutical manufacturer C1 which is a research client of the research project P1, to the doctor D1 who belongs to the research project P1.

As a start, the research client system 3 of the pharmaceutical manufacturer C1 transmits the document approval request information to the doctor D1 belonging to the research project P1 (step S20). The document approval request information is received by the data transfer server 30 associated with the research client system 3 of the pharmaceutical manufacturer C1. The data transfer server 30 transfers the received document approval request information to the data conversion server 20 (step S21).

Upon receipt of the document approval request information, the data conversion server 20: references the metadata stored in the storage unit 21; and converts a structure of the received document approval request information (a communication data) into a structure of a communication data commonly shared by the application servers 10 (step S22). That is, the data conversion server 20 converts information such as a destination, a source, a document type, or the like contained in the received document approval request information, into information such as a destination, a source, a document type, or the like, which are commonly shared in a plurality of the application servers 10.

The application server 10 having received the converted document approval request information creates a display which is to notify, for example, the doctor D1 of the receipt of the information in the "task" display window 522 on the landing page 52 (see FIG. 4) (for example, a display of "Approve BB report" in FIG. 4) (step S23). Note that what is performed by the application server 10 herein is only preparation of the display in the "task" display window 522 notifying the receipt of the document approval request information. An actual display thereof is performed by the researcher terminal 2.

When the doctor D1 logs in to the application server 10 of interest via the researcher terminal 2, the researcher terminal 2 being used by the doctor D1 displays therein the landing page 52 (see FIG. 4) with the "task" display window 522 thereon. Then, if the doctor D1 clicks, for example, a display portion saying "Approve report BB." in the "task" display window 522 (see FIG. 4), the researcher terminal 2 then displays a document approval request page (not illustrated) (step S24).

Next, when the doctor D1 performs an operation input for approving a document as requested via the document approval request page (step S25), the application server 10 transfers document approval completion information indicating that the document approval has been completed, to the data conversion server 20 (step S26). At this time, information such as a destination, a source, a document type, or the like is added to the document approval completion information.

The data conversion server 20 then: references the metadata stored in the storage unit 21; converts a structure of a communication data of the document approval completion information (containing information such as a destination, a source, an information type, or the like) transmitted from the application server 10, into a structure of a communication data used in the research client system 3 as the destination (step S27); and transfers the converted document approval completion information to the data transfer server 30.

The data transfer server 30 then transfers the document approval completion information transferred from the data conversion server 20, to the research client system 3 specified by the destination (step S28). In this way, the research client system 3 receives the document approval completion information from the doctor D1 to whom the document approval has been requested (step S29).

Note that a procedure similar to the described above is performed to a request for check or review a document. Such a request for review may be made to a plurality of persons in charge of the same research project. In that case, the request for review is transmitted to a plurality of the persons in charge, and a plurality of the persons in charge make respective responses.

Figure 8:
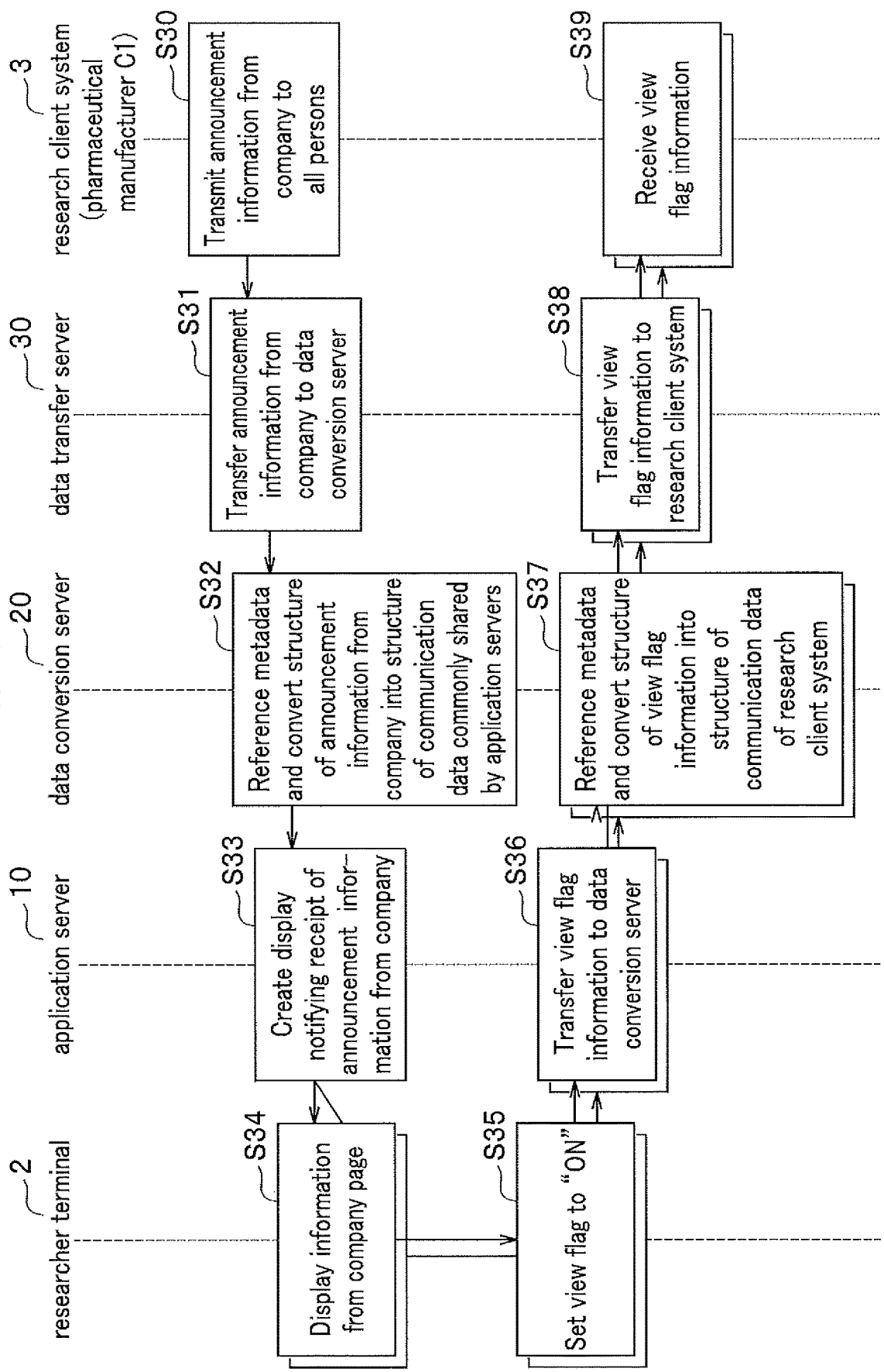
FIG. 8 is a diagram illustrating an example of a flow of an information processing performed when announcement information from a company is transmitted from the research client system to the researcher terminal.

FIG. 8 is a diagram illustrating an example of a flow of an information processing performed when announcement information from a company is transmitted from the research client system 3 to the researcher terminal 2. Below is described, with reference to FIG. 8, a case where announcement information (for example, "Application of CCCC clinical research is invited") is transmitted from the pharmaceutical manufacturer C1 which is a research client of the research project P1, to all persons in charge who belong to the research project P1.

As a start, the research client system 3 of the pharmaceutical manufacturer C1 transmits the announcement information to all persons in charge who belong to the research project P1 (step S30). The announcement information from the company is received by the data transfer server 30 associated with the research client system 3 of the pharmaceutical manufacturer C1. The data transfer server 30 transfers the received announcement information from the company, to the data conversion server 20 (step S31).

Upon receipt of the announcement information, the data conversion server 20: references the metadata stored in the storage unit 21; converts a structure of the received announcement information (a communication data) into a structure of a communication data commonly shared by the application servers 10 (step S32). That is, the data conversion server 20 converts information such as a destination, a source, a document type, or the like contained in the received announcement information from the company, into information such as a destination, a source, a document type, or the like, which are commonly shared in a plurality of the application servers 10.

The application server 10 having received the converted announcement information from the company creates a display which is to notify, for example, each of members of the research project P1 of the receipt of the information in the "information from companies" display window 524 on the landing page 52 (see FIG. 4) (for example, a display of "Application of CCCC clinical research is invited" in FIG. 4) (step S33). What is performed by the application server 10 herein is only preparation of the display in the "information from companies" display window 524 notifying the receipt of the announcement information from the company. An actual display thereof is performed by the researcher terminal 2.

When the person in charge belonging to the research project P1 logs in to the application server 10 of interest via the researcher terminal 2, the researcher terminal 2 being used by the person in charge displays therein the landing page 52 (see FIG. 4) with the "information from companies" display window 524 thereon. Then, if the person in charge clicks, for example, a display portion (see FIG. 4) saying "Application is invited for CCCC clinical research." in the "information from companies" display window 524, the researcher terminal 2 then displays an information from companies page regarding the CCCC clinical research (not illustrated) (step S34).

Then, when the person in charge performs an operation input by which it is confirmed that the person has viewed the page of the announcement information from the company, the application server 10 sets a view of the announcement information from the company to "ON" (step S35). The application server 10 transfers view flag information containing information that the view flag has been set to ON, to the data conversion server 20 (step S36).

The data conversion server 20 then: references the metadata stored in the storage unit 21; converts a structure of a communication data of the view flag information (containing information such as a destination, a source, an information type, or the like) transmitted from the application server 10 into a structure of a communication data used in the research client system 3 as the destination (step S37); and transfers the converted view flag information to the data transfer server 30.

The data transfer server 30 transfers the view flag information transferred from the data conversion server 20, to the research client system 3 specified by the destination (step S38). In this way, the research client system 3 receives the view flag information from the person in charge who has viewed the announcement information from the company (step S39).

The announcement information from the company described above is transmitted to all of the persons in charge belonging to the research project P1 and is thus viewed by a plurality of the persons in charge. This naturally means that the research client system 3 receives the view flag information from a plurality of the persons in charge. Though not explained herein, a procedure similar to the described above is performed to the news information as illustrated in FIG. 4 or the like.

As described above, in the clinical research information cloud service system 1 according to the embodiment of the present invention, the data conversion server 20 converts various types of information transmitted from each of the research client systems 3, into information commonly shared by the application servers 10. Note that the examples illustrated in FIG. 6 to FIG. 8 describe: that the data conversion server 20 converts the information such as a destination, a source, and an information type contained in the communication data transmitted from the research client system 3, into the information such as a destination, a source, and an information type commonly shared by the application servers 10; and that a conversion reverse to the described above is also made. Further description is, however, still required regarding conversion of the information type, and additional explanation is made below.

The information type of the task information (such as upload request information, document approval request information, and document review request information), news information, and announcement information from companies, as illustrated in FIG. 4, FIG. 5, or the like is the information type used in the application server 10 in this embodiment. As will be understood, the research client systems 3 have respective different information types having respective different names in many cases.

Thus, in this embodiment, the data conversion server 20 stores, in the storage unit 21, a data created by making the information type used in each of the research client systems 3 associate with the information type used in the application server 10, as a metadata. This makes it possible for the data conversion server 20 to convert the information type used in the research client system 3, into the information type used in the application server 10.

Note that the information type such as the task information, the news information, and the announcement information from companies as illustrated in FIG. 4, FIG. 5, or the like is given as a representative example, and any other information type may be used. The conversion of the information type described above can be regarded as a processing of classifying various information used in the research client system 3, by the information types defined in the application server 10.

As described above, in the embodiment of the present invention, the data conversion server 20 converts a structure of a communication data (such as a structure of a source, a destination, a name of a person in charge of research, and an information type) which varies depending on communications between a plurality of the research client systems 3, into a structure of a communication data commonly shared by the application servers 10; and a conversion reverse to the described above is also made. That is, the application server 10 can classify information transmitted from the research client system 3 based on a criteria for the application server 10. As a result, when the application server 10 receives information from the research client system 3, the application server 10 can provide the researcher terminal 2 with a display screen (a WEB display screen) independent of the research client system 3 in accordance with the classified information type.

As described above, a method of operating the researcher terminal 2 does not depend on the research client system 3. This means that, even when a person in charge of research who uses the researcher terminal 2 takes on a plurality of research projects from a plurality of research clients, it is not necessary for the person in charge to use a plurality of the different researcher terminals 2. Thus, even when the person in charge takes part in a plurality of different research projects from a plurality of different research clients, a workload of the person in charge can be prevented from increasing.

In this embodiment, the application server 10 is provided for each research project, and persons in charge belonging to the research project can commonly share a document. This makes it possible to facilitate sharing of information among the persons in charge of the research, and improvement in efficiency of research tasks can be expected.

DESCRIPTION OF REFERENCE NUMERALS 1 clinical research information cloud service system
2 researcher terminal
3 research client system
4, 4a, 4b communication network
10 application server
11 storage unit
12 back-end processing unit
13 front-end processing unit
20 data conversion server
21 storage unit
30 data transfer server
31 storage unit
51 login page
52 landing page
53 document upload page
111 user information storage unit
112 document storage unit
113 workflow information storage unit
114 notification information storage unit
121 user authentication unit
122 document management unit
123 workflow management unit
124 notification service management unit

The invention claimed is:

1. A clinical research information cloud service system, comprising:
    a plurality of application servers which are installed respectively corresponding to a plurality of clinical research projects and which are connected to a researcher terminal used by a person in charge of research of the clinical research project, via a communication network;
    a plurality of data transfer servers which are connected respectively corresponding to a plurality of research client systems used by respective research clients of a plurality of the clinical research projects; and
    a data conversion server which are connected to both a plurality of the data transfer servers and a plurality of the application servers and which includes a metadata for mutually associating a structure of a first communication data defined for each of a plurality of the research client systems and a structure of a second communication data commonly used by a plurality of the application servers, the data conversion server configured to, by referencing the metadata, mutually convert structures of the first and second communication data transmitted and received between the data transfer server and the application server.

2. The clinical research information cloud service system according to claim 1,
    wherein the application server is configured to: receive information transmitted from the research client system as the research client of the clinical research project to the person in charge of research belonging to the clinical research project, as information passing through the data transfer server and the data conversion server; and provide the researcher terminal with first display information which is information on a screen displaying the received information.

3. The clinical research information cloud service system according to claim 2,
wherein the data conversion server is configured to classify information transmitted from the research client system to the application server, by an information type commonly used by a plurality of the application servers.

4. The clinical research information cloud service system according to claim 3,
wherein, when the application server receives an input for login by a person in charge of research who has previously registered as a user, via the researcher terminal, the application server is configured to provide the researcher terminal with second display information which is information on a screen displaying, in an outlined manner, information which has been transmitted from the research client system to the person in charge of research and has been received by a time of the receipt of the input, the information being displayed also in a classified manner by the information type.

5. The clinical research information cloud service system according to claim 4,
wherein the application server has a storage unit which stores therein a document commonly shared by a plurality of user-registered persons in charge of research, and
wherein the application server is configured to, by referencing the storage unit, provide the researcher terminal with third display information which is information on a screen displaying a list of a title of a document commonly shared between the person in charge of research during the login and another person in charge of research.

6. A clinical research information cloud service method in a clinical research information cloud service system, the clinical research information cloud service system, comprising: a plurality of application servers which are installed respectively corresponding to a plurality of clinical research projects and which are connected to a researcher terminal used by a person in charge of research of the clinical research project, via a communication network; a plurality of data transfer servers which are connected respectively corresponding to a plurality of research client systems used by respective research clients of a plurality of the clinical research projects; and a data conversion server which are connected to both a plurality of the data transfer servers and a plurality of the application servers and which includes a metadata for mutually associating a structure of a first communication data defined for each of a plurality of the research client systems and a structure of a second communication data commonly used by a plurality of the application servers, the data conversion server configured to, by referencing the metadata, mutually convert structures of the first and second communication data transmitted and received between the data transfer server and the application server, the clinical research information cloud service method, comprising the steps, performed by the application server, of:
receiving information transmitted from the research client system as the research client of the clinical research project to the person in charge of research belonging to the clinical research project, as information passing through the data transfer server and the data conversion server; and
providing the researcher terminal with first display information which is information on a screen displaying the received information.

7. The clinical research information cloud service method according to claim 6, further comprising the step, performed by the data conversion server, of classifying information transmitted from the research client system to the application server, by an information type commonly used by a plurality of the application servers.

8. The clinical research information cloud service method according to claim 7, further comprising the step, performed by the application server, of,
when the application server receives an input for login by a person in charge of research who has previously registered as a user, via the researcher terminal,
providing the researcher terminal with second display information which is information on a screen displaying, in an outlined manner, information which has been transmitted from the research client system to the person in charge of research and has been received by a time of the receipt of the input, the information being displayed also in a classified manner by the information type.

9. The clinical research information cloud service method according to claim 5,
wherein the application server has a storage unit which stores therein a document commonly shared by a plurality of user-registered persons in charge of research,
the clinical research information cloud service system further comprising the step, performed by the application server, of, by referencing the storage unit, providing the researcher terminal with third display information which is information on a screen displaying a list of a title of a document commonly shared between the person in charge of research during the login and another person in charge of research.

* * * * *